United States Patent [19]
Yoo

[11] Patent Number: 5,549,960
[45] Date of Patent: Aug. 27, 1996

[54] MOXIBUSTING IMPLEMENT

[76] Inventor: Tae W. Yoo, 807, 1-Dong, Honyang, Apt. 32-5, Banpo-dong, Seocho-ku, Seoul, Rep. of Korea

[21] Appl. No.: 222,466

[22] Filed: Apr. 1, 1994

[30] Foreign Application Priority Data

Nov. 9, 1993 [KR] Rep. of Korea ............... 93-23351

[51] Int. Cl.$^6$ .................. B32B 3/24; A61F 7/00
[52] U.S. Cl. ............. 428/139; 428/138; 428/137; 428/913; 428/224; 604/291; 604/24; 604/304
[58] Field of Search ............... 428/138, 137, 428/40, 139, 913, 224; 604/291, 24, 304

[56] References Cited

U.S. PATENT DOCUMENTS 2,264,489  12/1941  Tiegler et al. ............... 428/136
3,946,733  3/1976  Han ............... 128/254
4,203,438  5/1980  Shiu ............... 128/254
4,325,371  4/1982  Atsumi ............... 128/254
4,604,088  8/1986  Nottbohm ............... 604/24
4,671,788  6/1987  Wu ............... 604/24
4,731,050  3/1988  Harada et al. ............... 604/24
4,747,841  5/1988  Kuratomi et al. ............... 604/291

FOREIGN PATENT DOCUMENTS 51536  7/1990  Rep. of Korea.

Primary Examiner—William Watkins
Attorney, Agent, or Firm—Richard M. Goldberg

[57] ABSTRACT

A moxibusting implement, which a moxa is inserted into an equal in size receiving hole of an upper paper-board and is adhered to an adhesion sheet having an adhesion layer. Thus, while a moxa is burned, the heat occurring is not emitted upwardly and flows down toward the receiving hole of the lower paper-board to enhance the effect of the moxa cautery treatment.

11 Claims, 1 Drawing Sheet

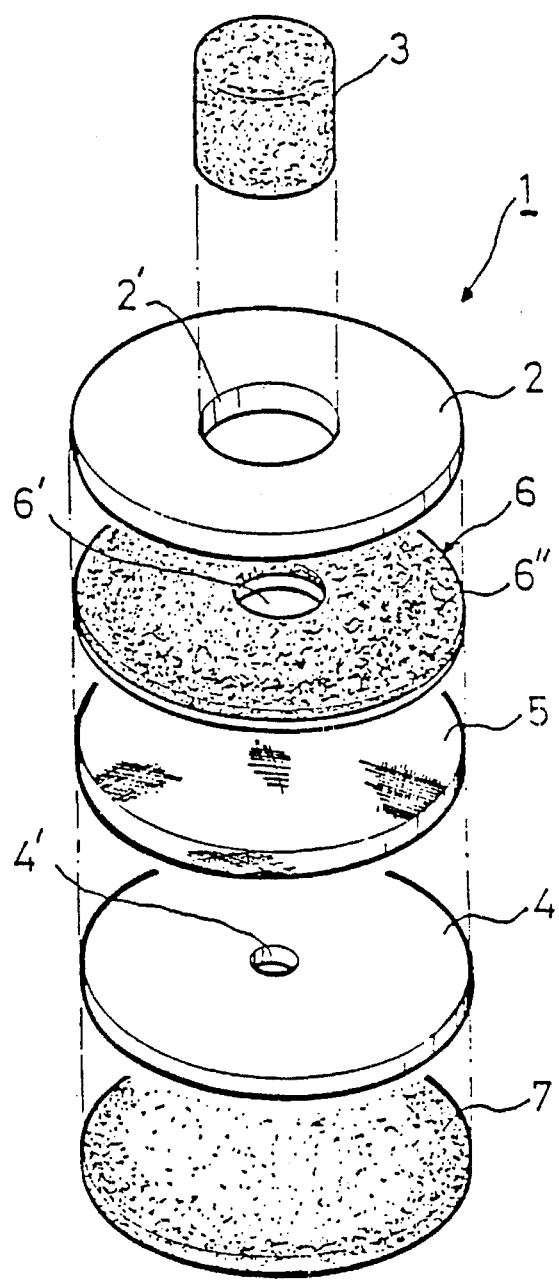
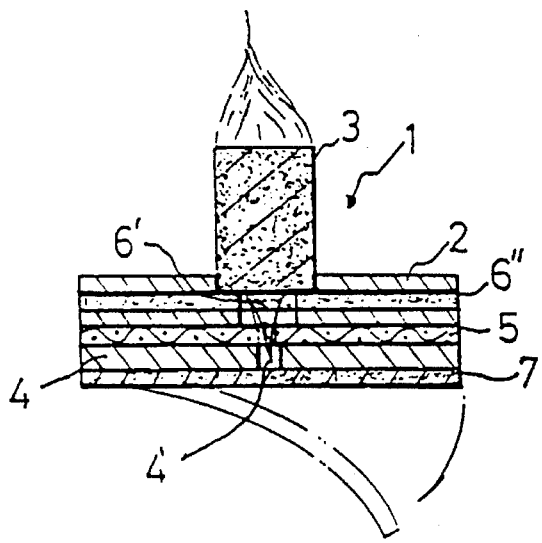
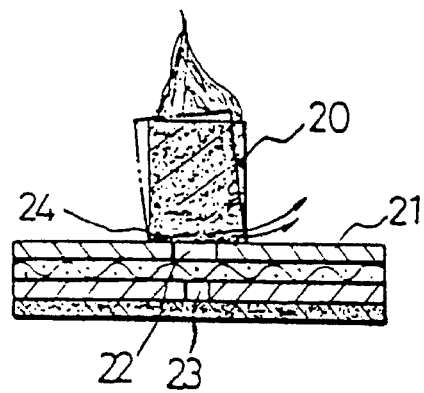

5,549,960

MOXIBUSTING IMPLEMENT

BACKGROUND OF THE INVENTION

1. Field of the Invention

The present invention relates to a moxibusting implement and more particularly this invention is an improvement over Korean Patent No. 51,536 of which I am an inventor.

2. Description of the Prior Art

In the said Patent No. 51,536 there is disclosed a moxibusting implement for moxa cautery. According to the said patent, to adhere a moxa the moxa is pasted on the upper paper-board. However, this process has a problem that the moxa may come off from the upper paper board because of the defect in its adhesion. Furthermore, as shown in FIG. 3, because of the difference in materials, in spite of adhesion of the moxa 20 on the upper paper-boa 21, there may have a gap between them. Thus, there is another problem that the effect of the moxa cautery treatment fails because the heat issuing with the moxa burning is emitted from the gap as well as receiving holes 22, 23.

SUMMARY OF THE INVENTION

One object of the present invention is to provide a moxibusting implement which can overcome the problems described above and to prevent the moxa from separating from the upper paper-board, by inserting the moxa into the receiving hole and securing the bottom of the moxa to the upperside of the adhesion sheet.

Another object of the present invention is to prevent the heat issuing with the moxa burning from releasing outwardly, by closely inserting it into the receiving hole.

BRIEF DESCRIPTION OF THE DRAWINGS

The other objects and features of the present invention will be hereinafter explained in detail with reference to the accompanying drawings, wherein:

FIG. 1 is an exploded perspective view of a moxibusting implement according to the invention, FIG. 2 is an assembled sectional view thereof, FIG. 3 is an assembled sectional view of a traditional moxibusting implement.

DESCRIPTION OF THE PREFERRED EMBODIMENTS

A moxa 3 is inserted into an equal size receiving hole 2' of an upper paper-board 2, and adhered to an adhesion sheet 6 having a smaller receiving hole 6' than one of the upper paper-board 2 and an adhesion layer 6" on the surface, thereof. A filter paper 5, a lower paper-board 4 and an exfoliation paper 7 are in order connected to the underside of adhesion sheet 6.

Referring to the drawings, reference numerals 1 and 4' designate a moxibusting implement and a receiving hole of the lower paper-board 4, which is smaller than hole 6 one of the adhesion sheet 6.

To summarize the advantages obtained by the invention, after removing the exfoliation paper 7 adhered to the lower paper-board 4 of the moxibusting implement 1, then adhering implement 1 to Meridian Points distributed at the skin surface, and igniting the moxa 3, the heat occurring flows into the receiving hole 2'. Thus, because the lower part of the moxa 3 is closely inserted into the receiving hole 2', the heat is not emitted upwardly and flows down toward the filter paper 5 through the receiving hole 6'.

The filter paper 5 is used to eliminate the wormwood resin and filter the heat passing through the sheet 6.

The filtered heat flows down toward the receiving hole 4', and thus Meridian Points on the skin are cauterized.

As mentioned above, this invention provides a moxibusting implement to enhance the effect of the moxa cautery treatment, by inserting and securing the moxa into the receiving hole 2' of the upper paper-board 2, thus preventing the heat from emitting outwardly as well as preventing the moxa 3 from separating from the upper paper-board 2.

What is claimed is:

1. A moxibusting implement comprising:

an upper paper-board having a receiving hole with a predetermined outer shape and dimension, and a lower surface, a moxa having a lower end with said predetermined outer shape and dimension, and closely fit within said receiving hole, said lower end having a lower surface, an adhesion sheet having an upper adhesion layer adhered to said lower surface of said upper paper-board and to said lower surface of said moxa, said adhesion sheet having a hole therein, a filter paper secured to a lower surface of said adhesion sheet, a lower paper-board secured to a lower surface of said filter paper and having a hole therein, and an exfoliation paper secured to a lower surface of said lower paper-board.

2. A moxibusting implement in accordance with claim 1, in which said hole of said adhesion sheet is smaller than the receiving hole of said upper paper-board.

3. A moxibusting implement in accordance with claim 1, in which said hole of said lower paper-board is smaller than the hole of said adhesion sheet.

4. A moxibusting implement in accordance with claim 2, in which said hole in said adhesion sheet is in alignment with said receiving hole of said upper paper-board.

5. A moxibusting implement in accordance with claim 3, in which said hole in said lower paper-board is in alignment with said hole in said adhesion sheet.

6. A moxibusting implement comprising:

an upper paper-board having a receiving hole with a predetermined outer shape and dimension, and a lower surface, a moxa having a lower end with said predetermined outer shape and dimension, and closely fit within said receiving hole, said lower end having a lower surface, an adhesion sheet having an upper adhesion layer adhered to said lower surface of said upper paper-board and to said lower surface of said moxa, said adhesion sheet having a hole therein; and at least one additional layer secured to a lower surface of said adhesion sheet.

7. A moxibusting implement in accordance with claim 6, in which said at least one additional layer includes:

a filter paper secured to a lower surface of said adhesion sheet; and a lower paper-board secured to a lower surface of said filter paper and having a hole therein.

8. A moxibusting implement in accordance with claim 7, in which said hole in said adhesion sheet is in alignment with said receiving hole of said upper paper-board and is of a smaller diameter than that of said receiving hole.

9. A moxibusting implement in accordance with claim 8, in which said hole in said lower paper-board is in alignment with said hole in said adhesion sheet and is of a smaller diameter than that of said hole in said adhesion sheet.

10. A moxibusting implement according to claim 1, wherein the predetermined outer shape is circular, and that the dimension is the diameter thereof.

11. A moxibusting implement according to claim 6, wherein the predetermined outer shape is circular, and that the dimension is the diameter thereof.

* * * * *

UNITED STATES PATENT AND TRADEMARK OFFICE
CERTIFICATE OF CORRECTION

PATENT NO. : 5,549,960
DATED : August 27, 1996
INVENTOR(S) : Tae Woo Yoo

It is certified that error appears in the above-indentified patent and that said Letters Patent is hereby corrected as shown below:

Title page, adjacent "[76] Inventor" change "Honyang" to --Hanyang--.

Column 1, line 17, change "paper-boa" to --paper-board--;
line 30, change "upperside" to -- upper side --;
line 58, change "6 one" to -- 6'--.

Column 2, line 4, after "the" (second occurrence) insert --adhesive--.

Signed and Sealed this

Thirty-first Day of December, 1996

Attest:

BRUCE LEHMAN

*Attesting Officer*       Commissioner of Patents and Trademarks